United States Patent [19]

Miller et al.

[11] Patent Number: 5,089,392
[45] Date of Patent: Feb. 18, 1992

[54] FLUOROGENIC SUBSTRATES FOR MEASUREMENT OF LYSOSOMAL ENZYME ACTIVITIES WITHIN INTACT CELLS

[75] Inventors: Stephen P. F. Miller; Roscoe O. Brady, both of Rockville, Md.

[73] Assignee: The United States of America as represented by of the Department of Health and Human Services, Washington, D.C.

[21] Appl. No.: 501,797

[22] Filed: Mar. 30, 1990

[51] Int. Cl.$^5$ .......................... C12Q 1/42; C12Q 1/02; G01N 31/00; G01N 35/08
[52] U.S. Cl. ........................................ 435/21; 435/18; 435/19; 435/29; 536/18.7; 536/55; 536/119; 514/524; 514/525; 560/138; 560/142; 560/145
[58] Field of Search .................... 435/18, 39, 4, 21, 5, 435/19, 29; 536/18.7, 55, 119; 560/138, 142, 145; 514/524, 525

[56] References Cited

U.S. PATENT DOCUMENTS

| | | | |
|---|---|---|---|
| 3,950,322 | 4/1976 | Thomas et al. | 435/18 |
| 4,242,447 | 12/1980 | Farid et al. | 435/39 |
| 4,659,657 | 4/1987 | Harnisch et al. | |
| 4,818,692 | 4/1989 | Rauscher et al. | 435/18 |
| 4,959,301 | 9/1990 | Weaver et al. | 435/5 |

OTHER PUBLICATIONS

Chemical Abstracts (1988) 109:139297q.
Chemical Abstracts (1989) 110:31853z.
Huxham et al., (1986) A Simple Visual Method for Assessing the Activation and Inhibition of Phenoloxidase Production by Insect Haemocytes in Vitro, *J. Immuno Meth* 94:271–7.
Musgrove et al., "Flow Cytometric Measurement . . . ," *Cytometry*, vol. 7, (1986), pp. 347–355.
Bieberich et al., "Intracellular Activity of Lysosomal . . . ," *Biol. Chem. Hoppe-Seyler*, vol. 70, (1989), pp. 809–817.
Jongkind et al., "Detection of Acid-$\beta$-Galactosidase . . . ," *Cytometry*, vol. 7, (1986), pp. 463–466.
Wittrup et al., "A Single-Cell Assay . . . ," *Cytometry*, vol. 9, (1988), pp. 394–404.
de Duve et al., "Lysosomotropic Agents," *Biochemical Pharmacology*, vol. 23, (1974), pp. 2495–2531.
Firestone et al., "Lysosomotropic Agents . . . ," *J. Med. Chem.*, vol. 22, (1979), pp. 1130–1133.
Brown et al., "Effect on pH on the Emission . . . ," *J. Chem. Soc. Farid, Trans. I*, (1977), pp. 1281–1285.
Dolbeare "Dynamic Assay of Enzyme Activity . . . ," *J. Histochem. Cytochem.*, vol. 27, No. 12, (1979), pp. 1644–1646.
Gillies et al., "Flow Cytometric Analysis . . . ," *Amer. J. Physiol.*, vol. 253, (1987), pp. C121–C125.
Ohkuma et al., "Fluorescence Probe Measurement . . . ," *Proc. Natl. Acad. Sci. U.S.A.*, vol. 75, No. 7, Jul. 1978, pp. 3327–3331.
Neufeld et al., *Annual Review of Biochemistry*, Inherited Disorders of Lysosomal Metabolism, vol. 44, (1975), pp. 357–376.

*Primary Examiner*—Robert A. Wax
*Assistant Examiner*—David R. Preston
*Attorney, Agent, or Firm*—Birch, Stewart, Kolasch & Birch

[57] ABSTRACT

Fluorogenic substrates and compositions containing the same are useful for detecting enzymatic activity within intact cells. The fluorogenic substrates are lysosomotropic derivatives of 2,3-dicyano-hydroquinone (DCH). These derivatives may be employed for detecting lysosomal enzymatic activity within intact cells using fluorescent microscopy and cytometry.

30 Claims, No Drawings

FLUOROGENIC SUBSTRATES FOR MEASUREMENT OF LYSOSOMAL ENZYME ACTIVITIES WITHIN INTACT CELLS

BACKGROUND OF THE INVENTION

1. Field of the Invention

The present invention relates to fluorogenic substrates and compositions containing the same useful for detecting the activity of enzymes within intact cells. More specifically, the present invention relates to lysosomotropic derivatives of 2,3-dicyano-hydroquinone (DCH), compositions containing the same and methods employing the same for detecting lysosomal enzymatic activity within intact cells.

2. Description of Related Art

Fluorogenic substrates that can be used to detect the activity of enzymes within intact cells are greatly desired for biochemical investigations of human metabolic storage disorders, and identification of gene transfer recombinants. These genetic diseases are caused by the lack of specific enzymes that normally function within lysosomes, which are intracellular membrane-bound organelles containing a variety of hydrolytic enzymes. While in vitro measurement using tissue or cellular extracts has become routine, the detection of enzymatic activity within living cells has proven to be more problematic. Two notable difficulties are the pH dependence of the fluorescence of some probes at physiological pH values (J. Slavik, *Intracellular pH and its measurement*, CRC Press, A. Ketyk and J. Slavik eds., Florida, (1989), pp. 87–126) and the undesirable tendency of the fluorescent product to diffuse out of the cells (Musgrove et al, *Cytometry*, vol. 7, (1986), pp. 347–355). Nevertheless, success has been achieved in some systems for example by cooling of the cells in order to slow efflux of the product, fixing of the fluorescent product as an insoluble precipitate or performing the incubations in microdroplets containing a single cell. A final, and more general, solution is the chemical modification of the fluorophore to obtain the desired properties (Yegoror et al, *Anal. Lett.*, 21, (1988), pp. 193–209; Sherman et al, *Anal. Chem.*, 40, (1968), pp. 803–805). A recent example is the synthesis of the 4-nonyl analog of 4-methyl-umbelliferone, and the study of its β-glucoside in normal and Gaucher fibroblasts (Beiberich et al, *Biol. Chem. Hoppe-Seyler*, vol. 370, (1989), pp. 809–817).

Other conventional fluorogenic substrates which have been used previously for lysosomal enzymatic activity detection include glycosides and esters of fluorescent phenols such as fluorescein (Jongkind et al, *Cytometry*, vol. 7, (1986), pp. 463–466) and resorufin (Wittrup et al, *Cytometry*, vol. 9, (1988), pp. 394–404. However, these conventional substrates are generally not optimal for in vivo measurements of enzyme activity and only a few fluorogenic substrates have been used within intact cells. Therefore, substrates that generate a fluorescent signal at intracellular pH conditions upon enzymatic hydrolysis are theoretically ideal and desirable since they exhibit high sensitivity and allow the living cells to be studied by accurate methods such as fluorescence microscopy. It is also desirable that the substrate exhibit lysosomotropic properties so that it is taken up selectively into lysosomes. Various lysosomotropic agents are known (de Duve et al, *Biochemical Pharmacology*, vol. 23, (1974), pp. 2495–2531; Firestone et al, *J. Med. Chem.*, vol. 22, (1979), pp. 1130–1133). However, the purposeful combination of a lysosomotropic substructure within a fluorogenic enzyme substrate has not been accomplished.

SUMMARY OF THE INVENTION

Therefore, it is an object of the present invention to provide fluorogenic substrates suitable for the measurement of enzymatic activity within intact cells.

It is another object of the present invention to provide fluorogenic substrates in which a portion of the molecule exhibits lysosomotropic properties so as to provide for concentration within lysosomes.

Another object of the present invention is to provide fluorogenic substrates which exhibit high fluorescence generated at physiological pH values down to the pH within lysosomes.

Yet a further object of the present invention is to provide fluorogenic substrates which permit the detection of small amounts of enzymatic hydrolysis in the presence of a large excess of the substrate.

Still a further object of the present invention is to provide fluorogenic substrates which are sufficiently hydrophobic so that they are readily taken up by intact living cells.

Yet a further object of the present invention is to provide compositions containing the fluorogenic substrates which may be used to detect lysosomal enzymatic activity.

Yet still a further object of the present invention is to provide methods for measuring lysosomal enzymatic activity which employ the fluorogenic substrates of the present invention.

The foregoing objects and others are accomplished in accordance with the present invention by providing fluorogenic substrates of the following formula:

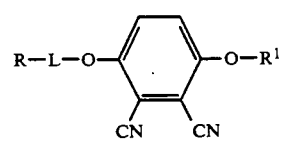

formula (I)

wherein R is a moderately basic acyclic, cyclic or aromatic amino group having a pKa of from about 4 to 9, L is a suitable linker which is stable to hydrolysis under enzyme assay conditions and $R^1$ is an enzyme substrate group.

The present invention further provides intermediates useful for synthesizing the substrates of formula (I) in which $R^1$ is hydrogen.

The present invention still further provides compositions containing the above-noted fluorogenic substrates of formula (I) along with appropriate carriers.

The present invention also provides methods for measuring lysosomal enzymatic activity in intact cells using the above-noted fluorogenic substrates of formula (I).

Further scope of the applicability of the present invention will become apparent from the detailed description. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The fluorogenic substrates of the present invention include 2,3-dicyano-hydroquinone (DCH) derivatives of the following formula:

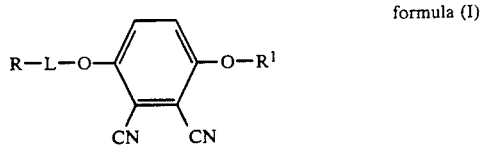

formula (I)

wherein R is a moderately basic acyclic, cyclic or aromatic amino group having a pKa of from about 4 to 9, L is a suitable linker which is stable to hydrolysis under enzyme assay conditions and $R^1$ is an enzyme substrate group. The R amino group is lysosomotropic because at the pH of the cytoplasm the R groups are predominantly uncharged, but in the acidic environment of the lysosomes they are predominantly charged, and thus become trapped inside the lysosomes.

Preferred fluorogenic substrates in accordance with the present invention include compounds of formula (I), wherein R is

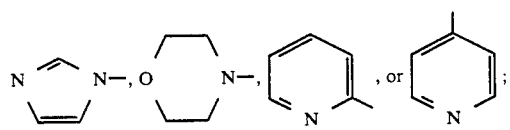

L is $-R^2-$ wherein $R^2$ is a straight or branched alkyl group of at least two carbon atoms which is substituted or unsubstituted (permissible substituents are any small organic or inorganic group that does not affect the enzyme hydrolysis reaction or adversely affect the rate of transmembrane diffusion, examples are $-OH$, halo, $-SH$, $-NH_2$, $-NH_2$ substituted with one or two $C_1-C_4$ branched or straight chain alkyl groups, $-CHO$, $-CO-(C_1-C_4$ alkyl), $-COO-$ $(C_1-C_4$ alkyl) or $-CONH_2$), an alkenyl group of at least four carbon atoms or an alkynyl group of at least four carbon atoms and $R^2$ may contain $-O-$, $-S-$ or

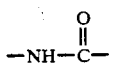

provided that there are at least two carbon atoms or a carbonyl group between any pair of heteroatoms; and $R^1$ is a glycosyl group, glycosyl group containing protecting groups, phosphorylcholine ester group, phosphate monoester group, sulfuric acid monoester group, or

wherein $R^3$ is an alkyl group or an alkenyl group or $R^3$ is

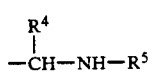

wherein $R^4$ is an amino acid side chain (formed from a naturally occuring amino acid including at least those found in plants and animals) and $R^2$ is hydrogen, an amino acid group bound through the carboxy group to form an amide linkage, a protecting group or a peptidyl group bound through its carboxy end to form an amide linkage. L is more preferably $-R^2-$ wherein $R^2$ is a straight or branched $C_2-C_{20}$ alkyl group, $C_4-C_{20}$ alkenyl group or $C_4-C_{20}$ alkynyl group. Non-limiting examples of the glycosyl protecting groups include acetate esters of alcohols and acetoxymethyl esters of carboxylates. Non-limiting examples of the protecting groups of $R^5$ include tert-butoxycarbonyl, benzyloxycarbonyl and benzoyl.

The present invention also encompasses intermediate compounds useful for synthesizing all of the above-noted fluorogenic substrates. These compounds include DCH derivatives of formula (I) wherein $R^1$ is hydrogen, and wherein R and L are each substituents corresponding to all of those noted above.

The present invention includes various advantageous features. For example, this is the first synthesis of the fluorophor 3 as shown in Scheme 1 below.

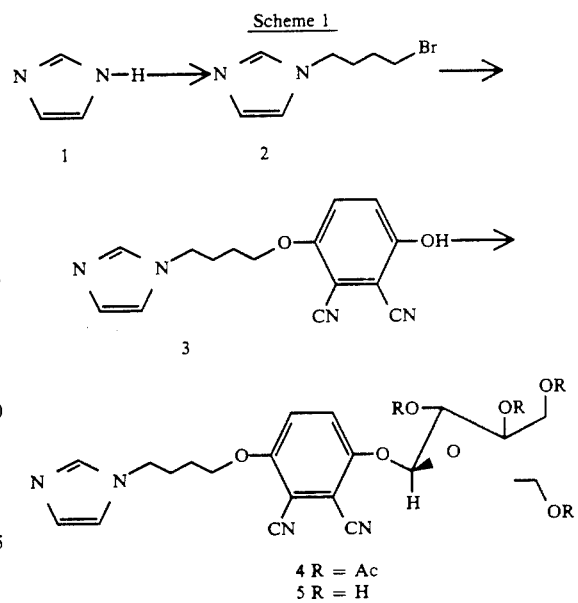

Nor have any derivatives of 3, e.g. compounds 4 or 5, been reported in the literature. The use of the compounds of the present invention or other fluorogenic substrates to detect lysosomal hydrolases within living cells with localization of these activities at the subcellular level is also significant. Two properties of the fluorogenic substrates of the present invention make this possible. Namely, (i) the subcellular targeting caused by the lysosomotropic amine portion of the molecule, and (ii) the physio-chemical properties of the fluorophor moiety (2,3-dicyano-phenol) that allow detection under physiological conditions. Another significant feature of the present invention is the purposeful inclusion of a lysosomotropic substructure within a fluorogenic enzyme substrate to target that substrate to lysosomes.

The route developed for the syntheses of the β-D-galactopyranoside of 2,3-dicyano-4-[4-(1-imidazolyl)-butoxy]-phenol 5 (Im-DCH-β-Gal) and Im-DCH-β-Gal(OAc)4 4 is outlined in Scheme 1. Experimental details of this preparation and the analytical characterization of the intermediates are given below. The phenol intermediate 3 is also the fluorophor that is released upon enzymatic hydrolysis of enzyme substrates such as 6 as shown in Scheme 2 below.

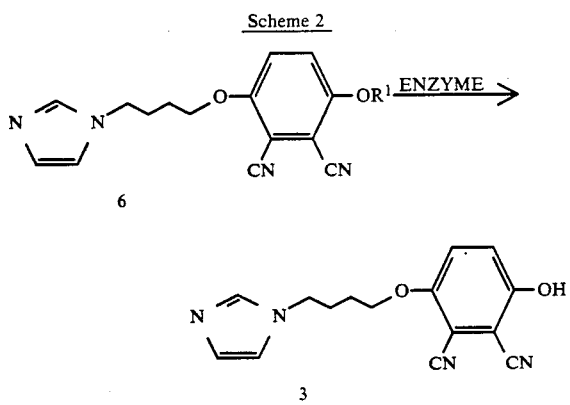

Scheme 2

Using known chemistry, the intermediate 3 is converted into many other potential enzyme substrates. These include other glycosides (glycosidase substrates), alkyl ethers (dealkylase substrates), carboxylic acid esters (esterase or peptidase substrates) and esters of inorganic acids (such as substrates for phosphatases, phosphodiesterases and sulfohydrolases).

The fluorogenic substrates of the present invention differ from previous examples in that a portion of the molecule exhibits "lysosomotropic" properties. This term refers to moderately basic amines that concentrate (via acid-base equilibria) in low pH organelles such as lysosomes. For Im-DCH in compounds 4 and 5, the N-alkyl imidazole moiety, with a pKa of approximately 7, serves this function. This lysosomotropic property accounts for a first important attribute of enzyme substrates based upon Im-DCH that is, concentration within lysosomes to ensure that sufficient substrate is concentrated within the lysosomes in order to yield a readily detectable fluorescent signal.

Two other advantages of the fluorophors of the present invention derive from their physical and optical properties: (1) The low pKa of the phenol in Im-DCH (pKa-5.6) allows the maximal fluoroscence (excitation at 385 nm, detection at 460 nm) to be generated at physiological pH values as well as the low pH conditions within lysosomes. The extremely low pKa of the excited state of Im-DCH (pKa*=0.5) permits strong fluorescence to be measured in solutions as acidic as pH 2-3. By proper choice of spectral parameters (excitation at 365 nm, detection at 460 nm), the fluorescence becomes essentially independent of pH, with a fluorescence intensity at pH 2 that is 60% of the maximum. Ratio measurements of fluorescence (emission at 460 nm with excitation at 365 and 385 nm) also provide an estimate of the pH at the site of enzymatic hydrolysis. (2) Shifts in both the absorption and emission spectra occur upon the hydrolysis of glycosides of Im-DCH to give free Im-DCH. This permits the detection of small amounts of enzymatic hydrolysis in the presence of a very large excess of substrate. For example, at 385 nm excitation and 460 nm detection, the ratio of fluoroescence of the hydrolysis product, Im-DCH, to intact Im-DCH-$\beta$-Gal is 620:1. Finally, the tetraacetate of Im-DCH-$\beta$-Gal is sufficiently hydrophobic so that is readily taken up by living cells. It is then deacetylated intracellularly to generate the enzymatically active substrate.

In formula (I), the R group comprises moderately basic amines which can be readily attached to DCH via a suitable linker. Examples of these amines include N-alkyl derivatives of imidazole and morpholine, or pyridine with alkyl substituents at the 2 or 4 position. The pKa of the amine moiety is from about 4 to 9 and preferably from about 6 to 8, for example about 7.

The requirements for the linker group include that it be available in a form which allows it to be covalently attached to the lysosomotropic amine group R and to the DCH moiety. For example, the linker may be an alipha, omega-dihalide or an omega-halo-aldehyde. A second requirement of the linker group is that it is chemically unreactive during the subsequent syntehtic steps. A third requirement is that it is stable to hydrolysis under the enzyme assay conditions. Organic groups which would fulfill the second and third requirements include alkyl or branched alkyl chains with at least two carbons between the oxygen of DCH and any heteroatoms in the R group. Carbon-carbon double or triple bonds, ethers, thioethers, ketones and amides may be employed as linker groups provided they fulfill the above requirements.

Synthetic routes for the alkylation of DCH with the lysosomotropic amines of formula (I) are as follows. Preparations are described for the saturated hexyl linker, wherein L is $-(CH_2)_6-$. In all cases, a three to five fold excess of the alpha, omega-dihalide is employed to reduce the formation of the by-product, "R-L-R".

Imidazole is deprotonated with sodium hydride in tetrahydrofuran and reacted with 1,6-dibromohexane. The reaction is quenched with acetic acid, and an excess of acetic acid is maintained with all of the intermediates of the form "R-L-Halogen" until they are reacted with DCH. Unless these halo-amides are stored as the protonated amine salt, they may rapidly decompose. The 6-(1-imidazolyl)-1-bromohexane acetate salt is then reacted with DCH in dimethyl formamide/acetone (9:1 vol/vol), using anhydrous potassium carbonate as the base. For this compound, and for all intermediates of the form "R-L-Halogen", a three fold excess of DCH and ten fold excess of potassium carbonate are employed to reduce the formation of the by-product in which both oxygens of DCH have been alkylated.

Morpholine may be alkylated with an excess of 1,6-dibromohexane in ethanol using potassium carbonate as a base. The intermediate halo-amine is stored as the protonated acetate salt, and then alkylated with DCH as described above.

The pyridine analogs are prepared from 2-methylpyridine or 4-methylpyridine. Lithiation with phenyllithium (for the 2-methyl isomer) or methyllithium (for the 4-methyl isomer) in dry hexane, followed by reaction with an excess of 1,5-dibromopentane gives the "R-L-Br" intermediate with a six carbon linker. The intermediate halo-amine is stored as the hydroacetate salt, and then alkylated with DCH as described above.

As shown below in Scheme 3, the intermediate alcohols 9 are converted into the fluorogenic substrate compounds of the present invention of formula (I).

Scheme 3

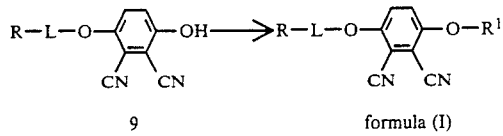

9          formula (I)

Listed below in Table 1 are compounds 10-15 which include various $R^1$ substituents.

TABLE 1

| Compound | $R^1$ Group |
| --- | --- |
| 10 | glycosyl |
| 11 | phosphorylcholine |
| 12 | $-PO_3H_2$ |
| 13 | $-SO_3H$ |
| 14 | $\begin{matrix} O \\ \parallel \\ -C-R^3 \end{matrix}$ |
| 15 | $\begin{matrix} R^4 \\ \mid \\ -CH-NH-R^5 \end{matrix}$ |

The glycosides of structure 10 are prepared from the aromatic alcohols 9. This alkylation is performed using 1-halo-sugars in which the remaining hydroxyl groups on the sugar are suitably protected. Examples of such saccharide protecting groups include the acetate or benzoate esters or benzyl ethers. Suitable halogens are the 1-bromo, and 1-chloro derivatives of the protected sugars; 2-chloro or 2-bromo derivatives are used in the case of neuraminic acids. The condensation of the phenol 9 or a metal salt or a tetraalkyl ammonium salt of the phenol with the halo-sugar occurs in anhydrous solvents such as toluene, methylene chloride, tetrahydrofuran or acetonitrile, or may occur under phase-transfer conditions, such as for example chloroform and aqueous sodium hydroxide. Inorganic catalysts such as silver carbonate, silver triflate, mercuric cyanide and others are added to promote the reaction and to control the stereochemistry of the glycosylation. Examples of the techniques for these glycosylations are described in H. Paulsen, *Angew. Chem. Int. Ed. Engl.*, 1982, 21, pp. 155-173. For neuraminic acids, and other sugars containing a carboxylic acid group, additional protecting groups such as methyl ethers of the acid group may be necessary. Suitable protecting groups and alkylation schemes for such acidic sugars are described in N. Baggett and B. arsden, *Carbohydrate Res.*, 1982, 110, pp. 11-18. Examples of such protecting groups include methyl, ethyl or benzyl esters of the carboxylic acid, as well as the acetate ester, benzoate ester and benzyl ether of the alcohol group.

The protecting groups are removed after the glycosylation by hydrolysis or hydrogenolysis. For example, acetates, benzoates and other esters are removed with sodium methoxide in methanol, benzyl ethers are removed with hydrogen in the presence of a palladium catalyst, and methyl esters are removed by hydrolysis in aqueous sodium hydroxide.

For in situ experiments in which penetration of cell membranes is required, the protecting groups may be retained on the carbohydrate portion of 10 to increase the hydrophobicity. Examples of these protecting groups include acetate esters of alcohols, and acetoxymethyl esters of carboxylates.

The phosphorylcholine ester 11 may be produced by coupling of 9 with the zwitterionic form of phosphorylcholine. Dicyclohexylcarbodiimide is an example of a suitable coupling reagent, and pyridine or anhydrous acetonitrile are examples of suitable solvents. Alternately, the phosphoric acid monoester 12 may be esterified with choline tosylate using dicyclohexylcarbodiimide in pyridine.

The phenol 9 may be converted to the phosphate monoester 12 by reaction with phosphorous oxytrichloride or phosphorous pentachloride in the presence of an acid scavenger such as pyridine or triethylamine. Examples of suitable solvents are anhydrous tetrahydrofuran, acetonitrile or pyridine. A tetraalkyl ammonium salt of 9 may be used for increased solubility in the reaction solvent. An excess of the phosphorous halide should be employed to avoid the formation of the phosphodiester of the aromatic alcohol. Hydrolysis of the phosphonyloxy dihalide intermediate can be affected by quenching the reaction with aqueous base, to give 12 as a salt. The free phosphonic acid monoester can be obtained by subsequent treatment with dilute mineral acid.

The sulfuric acid monoester 13 can be prepared from the phenol 9 by employing chlorosulfonic acid in a manner analogous to that described above for preparation of the phosphoric acid monoester.

Simple carboxylic acid esters 14 can be prepared from 9 by reaction with activated derivatives of the acid in pyridine, or in an inert solvent such as tetrahydrofuran containing pyridine or triethylamine. Suitable activated derivatives include anhydrides, acid chlorides and N-hydroxysuccinimide esters.

Amino acid and peptide esters denoted by structure 15 may be synthesized by acylation of 9 with suitably protected active esters of amino acids or peptides. Examples of suitable protecting groups include benzyloxycarbonyl, tert-butyloxycarbonyl, benzyl ether and other protecting groups employed in the chemical synthesis of peptides. Active esters might include the pentafluorophenol, N-hydroxysuccinimide, or N-hydroxybenzotriazole esters of the protected amino acid or peptide.

Examples of structures of the glycosyl and acyl portions of compounds 10-15 that provide specificity for a particular enzyme are listed in Table 2 below. Also listed is the lysosomal hydrolase, and the name of the genetic disease caused by deficiency of that enzyme.

TABLE 2

$$\text{R-L-O-}\underset{\underset{CN}{|}}{\overset{}{\bigcirc}}\text{-O-R}^1$$
(with CN at adjacent position)

| R$^1$ Group | Substrate of Lysosomal Hydrolase | Genetic Disease |
|---|---|---|
| (sugar structure: HO, OH, OH, OH) | β-D-Galactoside | G$_{M1}$ Gangliosidosis (β-Galactosidase Deficiency) Krabbe Disease (Galactosylceramidase Deficiency) |
| (sugar structure: HO, OH, OH, OH) | α-D-Galactoside | Fabry Disease (α-Galactosidase Deficiency) |
| (sugar structure with CH$_3$-C(=O)-NH, OH, OH) | α-D-N-Acetylgalactosaminide | Schindler Disease (α-N-Acetylgalactosaminidase Deficiency) |
| (sugar structure: HO, OH, OH, OH) | β-D-Glucoside | Gaucher Disease (Glucosylceramidase Deficiency) |
| (sugar structure with CH$_3$-C(=O)-NH, OH, OH) | β-D-N-Acetylglucosaminide | G$_{M2}$ Gangliosidoses (β-Hexoaminidase Deficiency) |
| (sugar structure with CH$_3$-C(=O)-NH, OH, OH) | β-D-N-Acetylgalactosaminide | G$_{M2}$ Gangliosidoses (β-Hexosaminidase Deficiency) |
| (sugar structure with CH$_3$-C(=O)-NH, OH, OH) | α-D-N-Acetylglucosaminide | Mucopolysaccharidoses Type III B (MPS III B) (α-N-Acetylglucosaminidase Deficiency) |
| (sugar structure: HO, OH, OH, CO$_2$H) | α-L-Iduronide | MPS I (α-L-Iduronidase Deficiency) |
| (sugar structure: HO, OH, OH, CO$_2$H) | β-D-Glucuronide | MPS IV (β-Glucuronidase Deficiency) |

TABLE 2-continued $$R-L-O-\underset{\underset{CN}{|}}{\overset{}{\bigcirc}}-O-R^1$$
(with CN groups on the benzene ring)

| R¹ Group | Substrate of Lysosomal Hydrolase | Genetic Disease |
|---|---|---|
| [α-D-mannopyranosyl structure with OH groups] | α-D-Mannoside | α-D-Mannosidase Deficiency |
| [β-D-mannopyranosyl structure with OH groups] | β-D-Mannoside | β-D-Mannosidase Deficiency |
| [α-L-fucopyranosyl structure with OH groups and CH₃] | α-L-Fucoside | α-L-Fucosidase Deficiency |
| [sialic acid structure with CO₂H, OH, NHC(O)CH₃, HO, OH] | α-D-N-Acetylneuraminide | α-Neuraminidase Deficiency |
| $-\overset{O}{\underset{\underset{O^{\ominus}}{\|}}{\overset{\|}{P}}}-O-CH_2CH_2-\overset{\oplus}{N}(CH_3)_3$ | Ester with Phosphorylcholine | Sphingomyelinase Deficiency |
| $-\overset{O}{\underset{\underset{O^{\ominus}}{\|}}{\overset{\|}{P}}}-O^{\ominus}$ | Phosphate Ester to measure Acid Phosphatase | |
| $-\overset{O}{\underset{\underset{O}{\|}}{\overset{\|}{S}}}-O^{\ominus}$ | Sulfate Ester to measure deficiencies of various sulfalases | Metachromatic Leukodystrophy Multiple Sulfatase Deficiency MPS II, MPS III A, MPS III D, MPS IV A, MPS VI |
| $-\overset{O}{\overset{\|}{C}}-R^3$ | Carboxylic Acid Esters: R³ = —CH₃ (acetate ester) R³ = —(CH₂)₇—CH=CH—(CH₂)₇CH₃ (oleic acid ester) | Acid Lipase Deficiency Wolman Disease Cholesterol Ester Storage Disease |
| $-\overset{O}{\overset{\|}{C}}-\underset{\underset{R^4}{\|}}{CH}-NH-R^5$ | Amino Acid Esters: R⁴ = amino acid side chain R⁵ = H, protecting group, amino acid or peptide (C-terminal ester of peptide is substrate for lysosomal peptidase or protease) | |

Also useful as $R^1$ groups in addition to those listed in Table 2 are the compounds in which the glycosyl portion has protecting groups on the free hydroxyl and carboxylate groups. Preferred are acetate groups on the hydroxyls and acetoxymethyl groups on the carboxylates. These protected glycosyl compounds are less polar than the unprotected glycosyl compounds and diffuse over the cell membrane more rapidly. The protecting groups are enzymatically removed in the cytoplasm by endogenous enzymes.

The fluorogenic substrates in accordance with the present invention may be formulated into various compositions with various suitable excipients or carriers such as those noted, for example, in U.S. Pat. No. 4,812,409 to Babb et al (issued Mar. 14, 1989) which is incorporated herein by reference. Depending upon their water solubilities, the substrates of this invention can be either dissolved directly in buffers or in a combination of buffer and water-miscible organic solvents, or solutions can be prepared containing a substrate, buffer, water-miscible organic solvent and surfactant.

When used for the determination of enzymes or organisms, the solution is buffered at 9 or less with one or more appropriate buffers. Useful buffers are readily determined by one skilled in the art and include phosphates, borates, and organic buffers as reported by Good et al in Biochem. 5,467 (1966) and Anal. Biochem 104,300 (1980). Preferably the solution is buffered to a pH of 8 or less. For measurement of lysosomal hydrolases in cell hydrolysates or other solutions, the pH may be buffered between pH 3 and 7, and preferably between pH 4 and 6.

Surfactants which are useful in the practice of this invention include any surfactants which do not inhibit compound hydrolysis. Generally, for detection of living cells, the useful surfactants are nonionic surfactants, including, for example, alkylarylpolyethoxy alcohols (e.g. Triton X-100 and X-305 available from Rohm & Haas, Philadelphia, Pa., p-alkylarloxy polyglycidols (e.g. SURFACTANT 10G available from Olin Corp., Stamford, Conn., USA), TWEEN 80 (available from ICI Americas, Inc., Wilmington, Del., USA), and others known to one skilled in the art.

Useful water-miscible organic solvents include alcohols (e.g. methanol, ethanol, propanol, etc.), N,N-dimethylformamide, dimethyl sulfoxide, acetonitrile, hexamethylenephosphoramide and the like. The particular solvent to be used for a particular substrate can be readily determined by routine experimentation.

A solution can be prepared in the following general manner. The substrate is dissolved in the water-miscible solvent at a concentration which depends upon its molecular weight, but generally at from about 1 to about 100, and preferably from about 5 to about 80, mg per ml of solvent. The resulting solution is then mixed with a suitable surfactant in an amount generally of from about 0.1 to about 24, and preferably from about 0.5 to about 10, mg surfactant per ml of solution. This preparation is generally carried out at room temperature.

The concentrated solution of substrate in the water-miscible solvent is then diluted with water or an aqueous buffer solution. The concentration of substrate in the final diluted solution is at least 0.01 millimolar, and preferably 1 to 100 millimolar. These solutions generally contain a buffer in an amount effective to maintain a physiological pH (9 or less). The concentration of buffer in the dispersion can vary widely, but is generally from about 0.01 to about 0.5 molar. Representative buffers are described above.

The determination of living cells, and particularly of bacterial cells, is often carried out in the presence of a nutrient for those cells although its presence is not essential. Any nutrient medium can be used which contains useful carbon, and optionally, nitrogen sources. Suitable nutrient medium having proper components and pH are well known in the art.

Some enzyme analytes require an inducer, i.e. a material or a combination of materials that promote the formation of the enzyme in the cell. The type of inducer or induction medium used is dependent upon the enzyme to be formed and determined. In some cases, both an inducer and a nutrient may be needed to promote formation. Another method of induction is to incubate the substrate in the presence of the nutrient for several minutes at appropriate temperatures prior to testing for the analyte.

The present invention is adaptable to either solution or dry assays. In a solution assay, a solution (or aqueous dispersion) containing a substrate can be prepared and contacted by mixing with a liquid test sample containing the living cells or hydrolytic analyte to be determined. Generally, the substrate is mixed with the test sample in a suitable container (e.g. test tube, petri dish beaker, cuvette, test device, etc.). The resulting solution (or dispersion) is gently mixed and incubated for a relatively short time (i.e. up to about 30 minutes) at a temperature up to about 40° C, and generally from about 20° C. to about 40° C. The test sample is then evaluated by measuring the resulting fluorescent dye with suitable detection equipment. Excitation wavelengths are in the range of 370 to 395 nm, and preferably between 385 and 395 nm. Emission is detected at 420 to 490 nm, preferably in the range of 460 to 475 nm.

The solution assay can also be carried out by contacting a porous absorbent material, e.g. paper strip, containing the test sample with a dispersion of the substrate. The analyte in the test sample can migrate from the porous material into the dispersion and initiate the analytical reactions needed for determination.

In solution assays, the amount of substrate present is at least about 0.01, and preferably from about 10 to about 100, millimolar. Other reagents needed for the assay can be present in amounts readily determined by one skilled in the art.

Alternatively, the method of this invention can be practiced using a dry analytical element. Such an element can be an absorbent carrier material, i.e. a thin sheet or strip of self-supporting absorbent or bibulous material, such as filter paper or strips, which contains the hydrolyzable substrate or a dried residue of a solution or dispersion comprising the same. Such elements are known in the art as test strips, diagnostic elements, dip sticks, diagnostic agents and the like.

Fluorogenic substrates may be introduced into cells in tissue culture by a variety of procedures. Conditions that have been optimized for loading Im-DCH-$\beta$-Gal-(OAc)$_4$ into human fibroblasts are described in the Examples below. In general, a solution or finely dispersed suspension of the substrate, or a suitable derivative of the substrate, is prepared in tissue culture medium. Appropriate derivatives might contain hydrophobic protecting groups such as acetates, acetoxymethyl esters or phosphonamides. Such derivatives are chosen for their ability to penetrate into the cells and then liberate the unprotected enzyme substrate by spontaneous or enzyme-catalysed hydrolysis. The substrate derivative or substrate may be directly dissolved in the cell culture medium, or a stock solution in a water-miscible solvent may be prepared and subsequently diluted into the medium. Suitable solvents are ethanol and dimethyl sulfoxide. To prevent damage to the living cells, the concentration of these solvents in the final medium should be limited to less than 3%, and preferably less than 0.5% (vol/vol). The final concentration of substrate derivative in the culture medium may fall in the range of 0.01 to 5 millimolar, and preferably 0.1 to 1 millimolar. Substrates may also be introduced into cells by techniques employing liposomes (Cutler et al, *Anal. Biochem.*, vol. 139, (1984), p. 482–486), protein complexes (Beiberich et al, *Biol. Chem. Hoppe-Seyler*, vol. 370, (1989), pp. 809–817) or reconstituted lipoproteins (Krieger et al, *J. Recept. Res.*, vol. 3, (1983), pp. 361–375). The cells are incubated with substrate for 15 minutes to 1 day, and may be subsequently incubated in fresh medium for an additional period of time.

Intracellular hydrolysis may be detected by scanning of a 96-well tissue culture plate with a fluorescence plate reader. Suitable devices are the Microfluor (Dynatech Labs., Chantilly, Va.) and the Cytofluor 2300 (Millipore Corp., Bedford, Mass.). The generation of the fluorescent product 3 (Scheme 3) is usually measured (at the wavelengths described above) subsequent to the loading, with the cells in fresh medium. By proper choice of wavelengths (excitation above 385 nm, emission at 460 to 500 nm), intracellular hydrolysis may be detected in the presence of excess substrate during the loading phase of the experiment.

Cells may also be grown on 8-well glass slides so that the uptake of substrate and its intracellular hydrolysis may be studied by fluorescence microscopy. Suitable wavelength bands for excitation may be obtained using interference filters (Omega Optical, Brattleboro, Vt.) and a xenon ar lamp. Appropriate filters and dichroic mirrors are also used to isolate the emitted light before recording of the images on photographic film or video tape. In addition to the detection of lysosomal hydrolases, fluorescence microscopy allows the subcellular localization of these enzymes to be studied. The fluorescence microscope may be equipped for spectroscopy by addition of scannable monochrometers for emission and/or excitation (Kurtz et al, *Biophys. J.*, vol. 48, (1985), pp. 499–508). This allows further information to be obtained, for example substrate: product ratios and pH measurements at the site of enzymatic hydrolysis.

Living cells loaded with substrate may also be studied with a flow cytometer or cell sorter (Wittrup et al, *Cytometry*, vol. 9, (1988), pp. 394–404). Using this technique, substrate hydrolysis may be measured on a cell-by-cell basis, and viable cells that display a particular level of enzymatic activity may be separated from the remainder of the cell population. This is particularly useful for selection of transfected cells in which the expression of a particular enzyme has been altered by genetic manipulation.

EXAMPLES

Synthesis of Substrates N-4-bromobutyl-imidazolium acetate 2

A 80% suspension of sodium hydride (2.36 g, 1.05 eq) was washed twice with THF under an atmosphere of argon. A solution of 5.1 g (75 mmole) of imidazole in 30 ml of THF was added to the stirring hydride, followed by an additional 130 ml of THF. The mixture was heated to reflux for 15 minutes, and then cooled to room temperature. After the rapid addition of 48.4 g (3 eq) of 1,4-dibromobutane, the thick mixture was stirred at room temperature for 18 hours. Acetic acid (8.6 ml, 2 eq) was added, and the solvent was removed under vacuum. Unreacted dibromide was removed by addition of 100 ml of 10% hydrochloric acid and extraction with chloroform (5×30 ml). The solution was then basified with solid sodium carbonate to pH 8, and the product was rapidly extracted with diethylether (5×75 ml). Acetic acid (4.3 ml, 1 eq) was added to the first ether extract, and subsequent extracts were pooled with it. The solvent was removed under vacuum, affording 10.6 g of product as a colorless oil. NMR analysis revealed the presence of 1.8 eq of acetate per mole of product, and confirmed a 45% yield of monosubstituted product. The remainder of the starting imidazole had been converted into by-products of higher polarity which are not extractable into diethylether. Storage of N-4-bromobutyl-imidazole as the free base results in the rapid formation of further quantities of these by-products. In contrast, no decomposition of the acetate salt was detected after several months at $-20°$ C.

TLC: chloroform/methanol/water (80:10:1), Rf=0.40 acetate salt, Rf=0.52 free amine.

H-1 NMR: DMSO-$d_6$=2.49 ppm: 7.67(1H,bs,Ar), 7.17(1H,d,J=1.0 Hz, Ar), 6.91(1H,bs,Ar), 4.00(2H,t,J=6.4 Hz,CH$_2$N), 3.51(2H,t,J=6.4 Hz,CH$_2$Br), 1.90(3H,s,CH$_3$CO$_2$), 1.8(4H,mult,CH$_2$CH$_2$), C-13 NMR: DMSO-$d_6$=39.5 ppm: 171.99, 137.13, 128.01, 119.30, 45.13, 34.18, 29.26, 29.16, 21.04.

IR: Neat (NaCl plate) 3130, 2940, 1715, 1550, 1370, 1250, 1080, 1005.

UV: $3.0\times10^{-4}$ M in ethanol 211 nm, $\epsilon=4.6\times10^3$ $M^{-1}Cm^{-1}$.

2,3-dicyano-4-[4-(1-imidazolyl)-butoxy]-phenol hydrochloride salt, 3

A suspension of anhydrous potassium carbonate (19.9 g) in 200 ml of 10% acetone in dimethyl formamide containing 6.92 g (43 mmole) of 2,3-dicyanohydroquinone was degassed under vacuum, backfilled with nitrogen, and magnetically stirred under nitrogen. A solution of 4.5 g of the acetate salt of N-4-bromobutyl-imidazole (14.5 mmole, containing 15 wgt % excess of acetic acid) in 12 ml of dimethyl formamide was added dropwise over 40 minutes. The resulting thick mixture was held at room temperature for 18 hours, after which the solvents were removed under vacuum (40 C, 1 mmHg). Water (50 ml) was added, followed by sufficient acetic acid (approx. 35 ml) to solubilize the product. After filtration through celite, the filtrate was brought to a pH of 7.5 with concentrated ammonium hydroxide to precipitate the product. Filtration and vacuum drying provided 10.3 g of yellow solids which contained the desired product. A 2.0 g portion of this crude product was heated with 20 ml of 1 M hydrochloric acid, and extracted while warm with ethyl acetate (3×25 ml). Upon cooling, the aqueous phase deposited crystals which were collected and washed with two 2 ml portions of cold 1.5 M hydrochloric acid. Vacuum drying provided 0.47 g of product as white needles, mp:250°–54° C. (calculated yield: 35%). Recrystallization from 1 M hydrochloric acid sharpened the melting point to 256°–257.5° C.

TLC: Rf=0.14 in chloroform/methanol/water (80:10:1), Rf=0.49 in chloroform/methanol/water (65:25:4).

H-1 NMR: HCl salt in 0.1M DCl/D$_2$O, DSS=0 ppm 8.76(1H,bs,Imid), 7.55(1H,t,J=1.7 Hz,Imid), 7.47(1H,t,J=1.7 Hz,Imid), 7.35(1H,d,J=9.6 Hz,Ar), 7.26(1H,d,J=9.6 Hz,Ar), 4.36(2H,t,J=7.0 Hz,CH$_2$O), 4.18(2H,t,J=5.8 Hz,CH$_2$N), 2.13(2H,p,J=7.3 Hz,CH$_2$CH$_2$O), 1.8(2H,mult,CH$_2$CH$_2$N).

IR: 4% in KBr 3050, 2240, 1577, 1545, 1500, 1450, 1290, 1075, 988, 833.

UV: $4.0 \times 10^{-4}$ M in 0.1 M sodium phosphate buffer pH=2: 347 nm, $\epsilon=5.4 \times 10^3$ M$^{-1}$cm$^{-1}$; 275 nm, $\epsilon=1.0 \times 10^3$ pH=12: 380nm, $\epsilon=5.7 \times 10^3$; 270nm, $\epsilon=8.6 \times 10^2$.

Analysis: C$_{15}$H$_{15}$ClN$_4$O$_2$ Calc. (Found); C:56.52(56.27), H:4.74(4.73), N:17.58(17.41).

Tetrabutylammonium salt of 2,3-dicyano-4-[4-(1-imidazolyl)-butoxy]-phenol

A suspension of 250 mg (0.78 mmol) of the hydrochloride salt, 3, in 4.3 ml of 0.2 M sodium hydroxide (1.1 eq) was added to 2 ml of chloroform and 0.56 g (1.1 eq) of aqueous tetrabutylammonium hydroxide (40 wgt %). After extraction of the fluorescent tetrabutylammonium salt into the chloroform, the aqueous phase was re-extracted with five 2 ml portions of fresh chloroform. The combined organic phases were dried over sodium sulfate, and the solvent was removed under vacuum to provide 489 mg of the strongly fluorescent salt as a yellow oil. This material was used within 24 hours in the subsequent alkylation reaction.

TLC: Rf=0.14 in chloroform/methanol/water (80:10:1),

H-1 NMR: N($^n$Bu)$_4$ salt in CDCl$_3$, TMS=0 ppm 7.50(1H,bs), 7.03(1H,bs), 6.97(1H,bs), 6.87(1H,d,J=9.6 Hz), 6.80(1H,d,J=9.6 Hz), 4.06(2H,t,J=7.1 Hz), 3.93(2H,t,J=5.9 Hz), 2.03(2H,p,J=7.3 Hz), 1.7(2H,m,J=6 Hz), counter-ion resonances: 3.26(8H,bt,J=8.0 Hz), 1.66(8H,mult), 1.43(8H,6-lines;J=7.1 Hz), 0.98(12H,t,J=7.1 Hz).

C-13 NMR: N($^n$Bu) salt, CDCl$_3$=77 ppm 168.20, 148.69, 137.02, 129.27, 128.30, 121.97, 118.97, 118.77, 115.68, 102.94, 97.93, 70.50, 46.63, 27.84, 26.19 Counter-ion resonances: 58.82, 23,86, 19.60, 13.51.

β-D-galactopyranoside of 2,3-dicyano-4-[4-(1-imidazolyl)-butoxy]-phenol-2,3,4,6-tetra-O-acetate, 4

The tetrabutyl ammonium salt of the starting material 3 (0.49 g, 0.8 mmol) was dissolved in 50 ml of acetonitrile containing 4 g of 3A molecular sieves under an atmosphere of dry nitrogen. Freshly prepared silver carbonate (0.43 g, 2 eq) was added, followed by 0.64 g of alpha-bromogalactose tetraacetate (2 eq). After stirring for 18 hours at room temperature, no starting phenol could be detected by TLC, and the suspension was filtered through celite. The filter cake was washed with four 6 ml portions of chloroform, which were combined with the acetonitrile and evaporated to dryness. The resulting 1.2 g of dark oil was dissolved in an 80:5 mixture of chloroform/methanol, and purified by flash chromatography over a silica gel column (3×23 cm). The column was eluted with chloroform/methanol (80:5), and the fractions between 130 mls and 270 mls were evaporated to give 0.42 g of galactoside (88% yield) as a slowly crystallizing oil. Recrystallization from ethanol provided 255 mg (53% yield) of white crystals. This material undergoes a phase change with partial melting at 115° C., recrystallizes at higher temperatures, and displays a sharp melting point at 169.5°-170° C. This behavior was not changed upon subsequent recrystallizations from ethanol.

TLC: R$_f$=0.36 in chloroform/methanol/water 80:10:1 R$_f$=0.73 in chloroform/methanol/water 65:25:4.

H-1 NMR: CDCL$_3$, TMS=0 ppm 7.52(2H,d,J=9.4 Hz,Ar), 7.50(1H,bs,Im), 7.10(2H,d,J=9.4 Hz,Ar), 7.06(1H,t,J=1Hz,Im), 6.96(1H,t,J=1Hz,Im), 5.54(1H,d of d,J=10.4,7.9 Hz,G2), 5.47(1H,d of d,J=3.4,0.9 Hz,G4), 5.10(1H, d of d,J=10.4,3.4 Hz,G3), 4.97(1H,d,J=7.9 Hz,G1), 4.3-4.0(3H,mult,G5&G6), 4.08(2H,t,J=7 Hz,OCH$_2$), 4.05(2H,t,J=5 Hz,NCH$_2$), 2.20(3H,s,Me), 2.16(3H,s,Me), 2.06(3H,s,Me), 2.05(2H,mult,CH$_2$), 2.02(3H,s,Me), 1.84(2H,mult,CH$_2$), C-13 NMR: CDCL$_3$=77 ppm 170.21, 170.03, 170.00, 169,41, CH$_3$CO$_2$; 157.28, 152.16,Arl&4; 137.08,Im2; 129.75, 118.69, Im4&5; 125.50, 117.88, Ar5&6; 112.50, 111.91, ArCN; 108.78, 105.30, Ar2&3; 101.43,Gl; 71.54, 70.40, G5&3; 69.50, ArOCH$_2$; 67.76, 66.62, G2&4; 61.11, G6; 46.57, NCH$_2$; 27.57, 25.98, CH$_2$CH$_2$; 20.85, 20.70, 20.67, 20.58, CH$_3$CO$_2$, IR: 4% in KBr 3340, 2940, 2230, 1755, 1487, 1370, 1240, 1065, 950, 905, 823, 740, UV: $3.0 \times 10^{-5}$ M in ethanol 220 nm, $\epsilon=3.8 \times 10^4$ M$^{-1}$cm$^{-1}$ 235 nm, $\epsilon=9.9 \times 10^3$; 334 nm; $\epsilon=6.9 \times 10^3$, Analysis: C$_{29}$H$_{32}$N$_4$O$_{11}$ Calc.(Found); C:56.86(56.60), H:5.26(5.26), N:9.15(9.05).

β-D-galactopyranoside of 2,3-dicyano-4-[4-(1-imidazolyl)-butoxy]-phenol, 5

Deprotection of the tetraacetate, 4, was readily accomplished by hydrolysis in methanolic sodium methoxide. Using 0.5 mmoles of sodium methoxide per mmole of 4, a two hour reaction at room temperature sufficed for complete deprotection. After neutralization with acetic acid (0.6 eq), the methanol was removed under vacuum. The resulting yellow solid was recrystallized from methanol to provide the free galactoside, 5, (melting point 190°-192° C.) in a 60% yield. Further recrystallization from ethanol sharpened the melting point to 193°-194.5° C.

TLC: R$_f$=0.03 in chloroform/methanol/water 80:10:1, R$_f$=0.20 in chloroform/methanol/water 65:25:4.

H-1 NMR: CDCL$_3$/CD$_3$OD, 1:1, TMS-0 ppm 7.62(1H,s,Im), 7.60(1H,d,J=9.5 Hz,Ar), 7.34(1H,d,J=9.5 Hz,Ar), 7.09(1H,s,Im), 6.99(1H,s,Im), 4.96(1H,d,J=7.6 Hz,Gl), 4.15(2H,t,J=5.5 Hz,NCH$_2$), 4.12(2H,t,J=7.1 Hz,OCH$_2$), 3.94(1H,bd,J=2.4 Hz,G4), 3.9-3.8(3H,mult,G3&G6), 3.68(1H,mult,G5), 3.59(1H,d of d,J=9.6,3.4 Hz,G3), 2.07(2H,mult,CH$_2$), 1.86(2H,mult,CH$_2$).

C-13 NMR: 0.04 M DCl in D$_2$O, CH$_3$OD=49 ppm 156.69,152.82,Arl&4; 134.46,Im2; 123.37,120.46,Ar5&6; 121.84,119.86,Im4&5; 114.11,113.78,ArCN; 04.58,102.98,Ar2&3; 101.29,Gl; 75.79,72.56,G5&3; 70.26,68.43,G2&4; 69.76,OCH$_2$; 60.89,G6; 49.12,NCH$_2$; 26.34,25.00,CH$_2$CH$_2$.

UV: $3.0 \times 10^{-5}$ M in pH 7 sodium phosphate buffer 339 nm, $\epsilon=6.5 \times 10^3$ M$^{-1}$cm$^{-1}$; 241 nm, $\epsilon=9.9 \times 10^3$; 225 nm, $\epsilon=3.6 \times 10^4$ Analysis: C$_{21}$H$_{24}$N$_4$O$_7$ Calc. (Found); C:56.75(56.65), H:5.44(5.50), N:12.61(12.35).

In vitro Examples

The ability of 5 to serve as a fluorogenic substrate was tested using fibroblasts derived from patients with GM1 gangliosidosis, a hereditary deficiency of lysosomal β-galactosidase. The unprotected galactoside, 5, was hydrolysed rapidly in vitro by lysates from three normal fibroblast lines, whereas lysates from four GM1 gangliosidosis lines displayed 0.3–5.3% of normal activity.

In vivo Examples

Loading of Im-DCH-β-Gal(OAc)., 4, into human skin fibroblasts in culture was accomplished as follows. A 20 mM solution of 4 in ethanol was injected via syringe into McCoy's medium to give a 0.1 mM final concentration of fluorogenic substrate. The substrate was further dispersed in the medium by sonication with a W140 Sonifier (two 10 second pulses on power setting of 3). After incubation for 24 hours in serum-free McCoy's medium, cells were loaded with 4 by replacement of the medium with medium containing 0.1 mM substrate. Excess Im-DCH-β-Gal(OAc) may be removed by rinsing the cells, after which the cells may be further incubated in serum free McCoy's medium. For fluorescence microscopy, the medium was replaced with Hank's balanced salt buffer, and cells grown on 8-well glass slides were observed with a filter set containing the following filters. Excitation (Xenon lamp) through a 360 nm bandpass filter with 10% transmittance at 310 and 385 nm. Emission through a chromatic beam splitter mirror that transmits fully above 405 nm plus a long pass filter with a transmittance of 1% at 408 nm and 10% at 412 nm. Enzymatic hydrolysis was followed by scanning of the loaded cells in a 96-well tissue culture plate with a Dynatech Microfluorometer. Quantitation of product formation was achieved by comparison of the fluorescence generated within individual wells with a standard curve that was obtained from known concentrations of the fluorescent product, 3.

The hydrophobic acetate, 4, was taken up by intact fibroblasts, where it is believed to be deacetylated to 5 prior to enzymatic hydrolysis since the acetylated derivative was inactive in cell-free systems that have β-galactosidase activity. Decreased activity was measured in GM1 cells (12–16% of normal) by fluorescence scanning of 96-well plates. This indicates that the B-galactosidase which acts in vivo is predominantly lysosomal. The intracellular localization of fluorescence in GMI fibroblasts treated with compound 4 suggests initial perinuclear clustering followed within 24 hours by sequestration into vacuoles. In contrast, normal cells are nonfluorescent 24 hours after loading, having hydrolysed their substrate and released the fluorescent product into the media. The impaired hydrolysis of 4 in GM1 gangliosidosis lines has been shown to be specific for their lysosomal β-galactosidase deficiency by comparison with cell lines expressing other lysosomal storage disorders.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. Compounds of the formula:

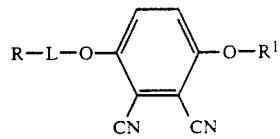

wherein R is a moderately basic acyclic, cyclic or aromatic amino group having a pKa of from about 4 to 9;

L is —R$^2$— which is a suitable linker that is stable to hydrolysis under enzyme assay conditions wherein R$^2$ is a straight or branched C$_2$-C$_{20}$ alkyl group which is substituted or unsubstituted, a C$_4$-C$_{20}$ alkenyl group or a C$_4$-C$_{20}$ alkynyl group and R$^2$ may contain —O—, —S— or

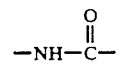

provided that there are at least two carbon atoms or a carbonyl group between any pair of heteroatoms; and R$^1$ is an enzyme substrate group which is a glycosyl group, glycosyl group containing one or more protecting groups, phosphorylcholine ester group, phosphate monoester group, sulfuric acid monoester group, or

wherein R$^3$ is an alkyl group or an alkenyl group or R$^3$ is

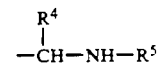

wherein R$^4$ is an amino acid side chain, and R$^5$ is hydrogen, an amino acid group bound through its α-carboxy group to form an aldehyde linkage, a protecting group or a peptidyl group bound through its α-carboxy end to form an amide linkage.

2. The compounds of claim 1, wherein L is —R$^2$— wherein R$^2$ is a straight or branched C$_2$-C$_{20}$ alkyl group which is unsubstituted or substituted with a member selected from the group consisting of —OH, halogen, —SH, —NH$_2$, —NH$_2$ substituted with one or two C$_1$-C$_4$ branched or straight chain alkyl groups, —CHO, —CO—(C$_1$-C$_4$ alkyl, —COO—(C$_1$-C$_4$ alkyl) and —CONH$_2$; a C$_4$-C$_{20}$ alkenyl group; or a C$_4$-C$_{20}$ alkynyl group and R$^2$ may contain —O—, —S— or

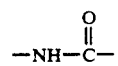

provided that there are at least two carbon atoms or a carbonyl group between any pair of heteroatoms.

3. The compounds of claim 1, wherein R$^1$ is a glycosyl group or a protected glycosyl group containing at least a protecting group, wherein said protecting group is an alkyl or benzyl ester of the carboxyl portion or is an acetate ester, benzoate ester or benzyl ether of the hydroxyl portion of said glycosyl group.

4. The compounds of claim 1, wherein R is

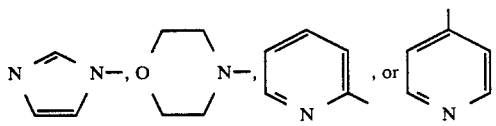

5. The compounds of claim 2, wherein $R^1$ is a glycosyl group selected from the group consisting of β-D-Galactoside, α-D-Galactoside, α-D-N-Acetylgalactosaminide, β-D-Glucoside, β-D-N-Acetylglucosaminide, β-D-N-Acetylgalactosaminide, α-D-N-Acetylglucosaminide, α-L-Iduronide, β-D-Glucuronide, α-D-Mannoside, β-D-Mannoside, α-L-Fucoside, and α-D-N-Acetylneuraminide.

6. The compounds of claim 2, wherein $R^1$ is a glycosyl group selected from the group consisting of β-D-Galactoside, α-D-Galactoside, α-D-N-Acetylgalactosaminide, β-D-Glucoside, β-D-N-Acetylglucosaminide, β-D-N-Acetylgalactosaminide, α-D-N-Acetylglucosaminide, α-L-Iduronide, β-D-Glucuronide, α-D-Mannoside, β-D-Mannoside, α-L-Fucoside, and α-D-N-Acetylneuraminide, wherein the free hydroxyl groups in the glycosyl groups are acetylated and the carboxylate groups are esterified with acetoxymethanol.

7. The compounds of claim 2, wherein $R^1$ is a substrate of a lysosomal hydrolase and is selected from the group consisting of

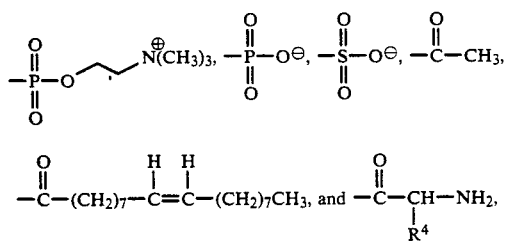

wherein $R^4$ is an amino acid side chain.

8. The compounds of claim 2, wherein L is $-R^2-$ and $R^2$ is a member selected from the group consisting of a straight or branched $C_2-C_{20}$ alkyl group, $C_4-C_{20}$ alkenyl group and $C_4-C_{20}$ alkynyl group.

9. Compounds of the formula:

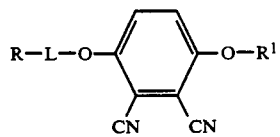

wherein R is a moderately basic acyclic, cyclic or aromatic amino group having a pKa of from about 4 to 9;
L is $-R^2-$ which is a suitable linker that is stable to hydrolysis under enzyme assay conditions wherein $R^2$ is a straight or branched $C_2-C_{20}$ alkyl group which is substituted or unsubstituted, a $C_4-C_{20}$ alkenyl group or a $C_4-C_{20}$ alkynyl group and $R^2$ may contain $-O-$, $-S-$ or

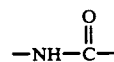

provided that there are at least two carbon atoms or a carbonyl group between any pair of heteroatoms; and
$R^1$ is hydrogen.

10. The compounds of claim 9, wherein R is

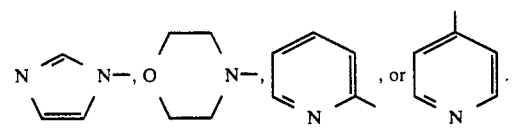

11. The compounds of claim 3, wherein L is $-R^2-$ wherein $R^2$ is a straight or branched $C_2-C_{20}$ alkyl group which is unsubstituted or substituted with a member selected from the group consisting of $-OH$, halogen, $-SH$, $-NH_2$, $-NH_2$ substituted with one or two $C_1-C_4$ branched or straight chain alkyl groups, $-CHO$, $-CO-(C_1-C_4$ alkyl), $-COO-(C_1-C_4$ alkyl) and $-CONH_2$; a $C_4-C_{20}$ alkenyl group; or a $C_4-C_{20}$ alkynyl group and $R^2$ may contain $-O-$, $-S-$ or

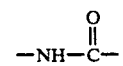

provided that there are at least two carbon atoms or a carbonyl group between any pair of heteroatoms.

12. The compounds of claim 9, wherein L is $-R^2-$ and $R^2$ is a member selected from the group consisting of a straight or branched $C_2-C_{20}$ alkyl group, $C_4-C_{20}$ alkenyl group and $C_4-C_{20}$ alkynyl group.

13. Compositions for introduction into intact, living cells for measuring enzymatic activity which comprises a suitable excipient and a compound of the formula:

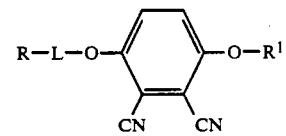

wherein R is a moderately basic acyclic, cyclic or aromatic amino group having a pKa of from about 4 to 9;
L is $-R^2-$ which is a suitable linker that is stable to hydrolysis under enzyme assay conditions wherein $R^2$ is a straight or branched $C_2-C_{20}$ alkyl group which is substituted or unsubstituted, a $C_4-C_{20}$ alkenyl group or a $C_4-C_{20}$ alkynyl group and $R^2$ may contain $-O-$, $-S-$ or

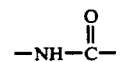

provided that there are at least two carbon atoms or a carbonyl group between any pair of heteroatoms; and
$R^1$ is an enzyme substrate group which is a glycosyl group, glycosyl group containing one or more protecting groups, phosphorylcholine ester group, phosphate monoester group, sulfuric acid monoester group, or

wherein $R^3$ is an alkyl group or an alkenyl group or $R^3$ is

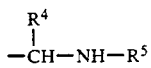

wherein $R^4$ is an amino acid side chain, and $R^5$ is hydrogen, an amino acid group bound through its α-carbon group to form an amide linkage, a protecting group or a peptidyl group bound through its α-carboxy end to form an amide linkage.

14. The compounds of claim 13, wherein L is —$R^2$— wherein $R^2$ is a straight chain or branched $C_2$-$C_{20}$ alkyl group which is unsubstituted or substituted with a member selected from the group consisting of —OH, halogen, —SH, —$NH_2$, —$NH_2$ substituted with one or two $C_1$-$C_4$ branched or straight chain alkyl groups, —CHO, —CO—($C_1$-$C_4$ alkyl), —COO—($C_1$-$C_4$ alkyl) and —$CONH_2$; a $C_4$-$C_{20}$ alkenyl group; or a $C_4$-$C_{20}$ alkynyl group and $R^2$ may contain —O—, —S— or

provided that there are at least tow carbon atoms or a carbonyl group between any pair of heteroatoms.

15. The compositions of claim 13, wherein $R^1$ is a glycosyl group selected from the group consisting of β-D-Galactoside, α-D-Galactoside, α-D-N-Acetylgalactosaminide, β-D-Glucoside, β-D-N-Acetylglucosaminide, β-D-N-Acetylgalactosaminide, α-D-N-Acetylglucosaminide, α-L-Iduronide, β-D-Glucuronide, α-D-Mannoside, β-D-Mannoside, α-L-Fucoside, and α-D-N-Acetylneuraminide.

16. The compositions of claim 13, wherein $R^1$ is a glycosyl group selected from the group consisting of β-D-Galactoside, α-D-Galactoside, α-D-N-Acetylgalactosaminide, β-D-Glucoside, β-D-N-Acetylglucosaminide, β-D-N-Acetylgalactosaminide, α-D-N-Acetylglucosaminide, α-L-Iduronide, β-D-Glucuronide, α-D-Mannoside, β-D-Mannoside, α-L-Fucoside, and α-D-N-Acetylneuraminide, wherein the free hydroxyl groups in the glycosyl groups are acetylated and the carboxylate groups are esterified with acetoxymethanol.

17. The compositions of claim 13, wherein $R^1$ is a substrate of a lysosomal hydrolase and is selected from the group consisting of

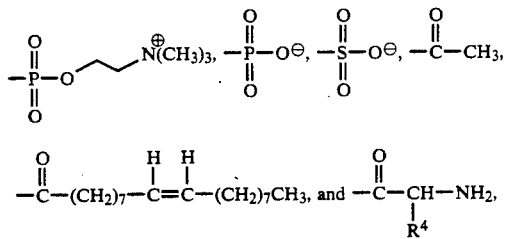

wherein $R^4$ is an amino acid side chain.

18. The compositions of claim 13, wherein $R^1$ is a glycosyl group or a protected glycosyl group containing at least a protecting group, wherein said protecting group is an alkyl or benzyl ester of the carboxyl portion or is an acetate ester, benzoate ester or benzyl ether of the hydroxyl portion of said glycosyl group.

19. The compositions of claim 13, wherein said excipient is an aqueous buffer solution, water-miscible organic solvent, surfactant or a mixture thereof.

20. The compositions of claim 13, wherein the concentration of said compound is from 1 to 100 millimolar.

21. A method for measuring enzymatic activity within intact, living cells which comprises administering to said cells a composition comprising a suitable excipient and a compound of the formula:

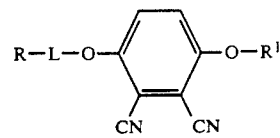

wherein R is a moderately basic acyclic, cyclic or aromatic amino group having a pKa of from about 4 to 9; L is —$R^2$— which is a suitable linker that is stable to hydrolysis under enzyme assay conditions wherein $R^2$ is a straight or branched $C_2$-$C_{20}$ alkyl group which is substituted or unsubstituted, a $C_4$-$C_{20}$ alkenyl group or an alkynyl group and $R^2$ may contain —O—, —S— or

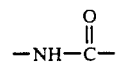

provided that there are at least two carbon atoms or a carbonyl group between any pair of heteroatoms; and $R^1$ is an enzyme substrate group which is a glycosyl group, glycosyl group containing one or more protecting groups, phosphorylcholine ester group, phosphate monoester group, sulfuric acid monoester group, or

wherein $R^3$ is an alkyl group or an alkenyl group or $R^3$ is

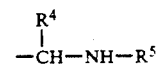

wherein $R^4$ is an amino acid side chain, and $R^5$ is hydrogen, an amino acid group bound through its α-carboxy group to form an amide linkage, a protecting group or a peptidyl group bound through its α-carboxy end to form an amide linkage; and measuring the fluorescence exhibited by the administered composition within the cells to determine enzymatic activity therein.

22. The method of claim 10, wherein the fluorescence is measured using a fluorescence microscope, flow cytometer or cell sorter.

23. The method of claim 21, wherein L is —$R^2$— wherein $R^2$ is a straight or branched $C_2$-$C_{20}$ alkyl group which is unsubstituted or substituted with a member selected from the group consisting of —OH, halogen, —SH, —$NH_2$, —$NH_2$ substituted with one or two $C_1$-$C_4$ branched or straight chain alkyl groups, —CHO, —CO—($C_1$-$C_4$ alkyl), —COO—($C_2$-$C_4$ alkyl) and —$CONH_2$; a $C_4$-$C_{20}$ alkenyl group; or a $C_4$-$C_{20}$ alkynyl group and $R^2$ may contain —O—, —S— or

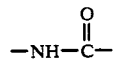

provided that there are at least two carbon atoms or a carbonyl group between any pair of heteroatoms.

24. The method of claim 21, wherein R¹ is a glycosyl group selected from the group consisting of β-D-Galactoside, α-D-Galactoside, α-D-N-Acetylgalactosaminide, β-D-Glucoside, β-D-N-Acetylglucosaminide, β-D-N-Acetylgalactosaminide, α-D-N-Acetylglucosaminide, α-L-Iduronide, β-D-Glucuronide, α-D-Mannoside, β-D-Mannoside, α-L-Fucoside, and α-D-N-Acetylneuraminide.

25. The method of claim 21, wherein R¹ is a glycosyl group selected from the group consisting of β-D-Galactoside, α-D-Galactoside, α-D-N-Acetylgalactosaminide, β-D-Glucoside, β-D-N-Acetylglucosaminide, β-D-N-Acetylgalactosaminide, α-D-N-Acetylglucosaminide, α-L-Iduronide, β-D-Glucuronide, α-D-Mannoside, β-D-Mannoside, α-L-Fucoside, and α-D-N-Acetylneuraminide, wherein the free hydroxyl groups in the glycosyl groups are acetylated and the carboxylate groups are esterified with acetoxymethanol.

26. The method of claim 21, wherein R¹ is a substrate of a lysosomal hydrolase and is selected from the group consisting of

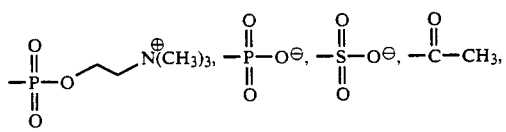

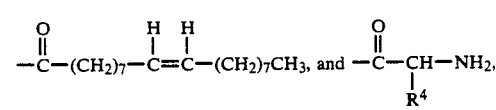

wherein R⁴ is an amino acid side chain.

27. The method of claim 21, wherein R¹ is a glycosyl group or a protected glycosyl group containing at least a protecting group, wherein said protecting group is an alkyl or benzyl ester of the carboxyl portion or is an acetate ester, benzoate ester or benzyl ether of the hydroxyl portion of said glycosyl group.

28. The method of claim 21, wherein said excipient is an aqueous buffer solution, water-miscible organic solvent, surfactant or a mixture thereof.

29. The method of claim 21, wherein the concentration of said compound in said composition is from 1 to 100 millimolar.

30. The method of claim 21, wherein said cells are in a tissue culture.

* * * * *